US012053576B2

(12) United States Patent
Chang et al.

(10) Patent No.: US 12,053,576 B2
(45) Date of Patent: Aug. 6, 2024

(54) NEBULIZER DEVICE AND NOZZLE MODULE

(71) Applicant: HCMed Innovations Co., LTD., Taipei (TW)

(72) Inventors: Chia-Chien Chang, New Taipei (TW); Yuan-Ming Hsu, New Taipei (TW)

(73) Assignee: HCMed Innovations Co., LTD., Taipei (TW)

( * ) Notice: Subject to any disclaimer, the term of this patent is extended or adjusted under 35 U.S.C. 154(b) by 558 days.

(21) Appl. No.: 17/373,738

(22) Filed: Jul. 12, 2021

(65) Prior Publication Data

US 2022/0305221 A1    Sep. 29, 2022

(30) Foreign Application Priority Data

Mar. 24, 2021    (TW) .................................. 110110579

(51) Int. Cl.
*A61M 15/00* (2006.01)
*B05B 7/10* (2006.01)

(52) U.S. Cl.
CPC ...... *A61M 15/0021* (2014.02); *A61M 15/002* (2014.02); *A61M 15/009* (2013.01); *B05B 7/10* (2013.01)

(58) Field of Classification Search
CPC ......... B05B 1/002; B05B 7/2424; B05B 7/10; A61M 11/001; A61M 2205/3331; A61M 15/0086; A61M 15/002; A61M 15/0021; A61M 15/009
See application file for complete search history.

(56) References Cited

U.S. PATENT DOCUMENTS

| 5,692,493 A * | 12/1997 | Weinstein ......... A61M 15/0021 |
| | | 128/200.14 |
| 2003/0136399 A1* | 7/2003 | Foley .................. A61M 11/002 |
| | | 128/200.14 |
| 2010/0319687 A1* | 12/2010 | Esaki ................ A61M 15/0018 |
| | | 128/200.23 |

(Continued)

FOREIGN PATENT DOCUMENTS

| CN | 209316733 U | 8/2019 |
| CN | 211461405 U | 9/2020 |

(Continued)

*Primary Examiner* — Christopher R Dandridge
(74) *Attorney, Agent, or Firm* — Li & Cai Intellectual Property Office (57) ABSTRACT

A nebulizer device and a nozzle module are provided. The nebulizer device includes a nebulizer module, the nozzle module, and a control module. The nozzle module includes a main body unit and a guide unit. The main body unit can be detachably connected to the nebulizer module. The main body unit has a plurality of openings penetratingly formed therethrough, an accommodating space, and an output part, and the openings and the output part are in spatial communication with the accommodating space. The main body unit corresponds to an inner wall of the accommodating space and protrudes toward the accommodating space to form a plurality of guiding parts, and each of the guiding parts is adjacent to one of the openings. The guide unit is disposed in the accommodating space and has a recessed part. The control module can be detachably connected to the main body unit.

14 Claims, 10 Drawing Sheets

(56) References Cited

U.S. PATENT DOCUMENTS

2014/0230811 A1\* 8/2014 Von Hollen .......... A61M 11/06
　　　　　　　　　　　　　　　　　　　　　128/200.14
2018/0311156 A1\* 11/2018 Yadidi ............... A61M 15/0045

FOREIGN PATENT DOCUMENTS

| CN | 211798071 U | 10/2020 | | |
|---|---|---|---|---|
| TW | M534609 U | 1/2017 | | |
| WO | WO2014019563 A1 | 2/2014 | | |
| WO | WO-2017093966 A1 | \* | 6/2017 | .......... A61M 15/002 |
| WO | WO-2019237151 A1 | \* | 12/2019 | .......... A61K 31/573 |

\* cited by examiner

NEBULIZER DEVICE AND NOZZLE MODULE

CROSS-REFERENCE TO RELATED PATENT APPLICATION

This application claims the benefit of priority to Taiwan Patent Application No. 110110579, filed on Mar. 24, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a nebulizer device and a nozzle module, and more particularly to a nebulizer device and a nozzle module that can reduce aggregation, collision, and condensation of atomized particles and improve aerosol guiding efficiency.

BACKGROUND OF THE DISCLOSURE

A nebulizer device is widely used in various industries, such as for purposes of cooling, humidification, disinfection, dust suppression, and medical applications. For example, when the nebulizer device is used as a medical inhaler device, a particle size of a nebulized liquid drug must be smaller than 3 μm to 5 μm to ensure that the drug can effectively reach the lower respiratory tract and be directly absorbed by a human body, so as to improve an effectiveness of the treatment with the drug.

In order to improving an atomized particle delivery efficiency of a conventional nebulizer device, holes are created on the nebulizer device to introduce external air into the nebulizer device. However, air guiding structures are not provided inside of the nebulizer device, and the holes on the nebulizer device are not designed to guide aerosol flow. Therefore, a turbulent flow is generated when the external air enters into the nebulizer device through the holes, which causes atomized particles to easily aggregate and collide with one another and condense into large liquid droplets, so that a delivery of a final output of the nebulized liquid drug to the human body is reduced.

Therefore, how to overcome the abovementioned shortcomings through an improvement of a structural design of the nebulizer device and the nozzle module has become one of the important issues to be solved in this industry.

SUMMARY OF THE DISCLOSURE

In response to the above-referenced technical inadequacy, the present disclosure provides a nebulizer device and a nozzle module.

In one aspect, the present disclosure provides a nebulizer device, which includes a nebulizer module, a nozzle module, and a control module. The nozzle module includes a main body unit and a guide unit. The main body unit can be detachably connected to the nebulizer module. The main body unit has a plurality of openings penetratingly formed through the main body unit, an accommodating space, and an output part, and the openings and the output part are in spatial communication with the accommodating space. The main body unit corresponds to an inner wall of the accommodating space and protrudes toward the accommodating space to form a plurality of guiding parts, and each of the guiding parts is adjacent to one of the openings. The guide unit is disposed in the accommodating space and has a recessed part. The control module can be detachably connected to the main body unit.

In another aspect, the present disclosure provides a nozzle module, which includes a main body unit and a guide unit. The main body unit has a plurality of openings penetratingly formed through the main body unit, an accommodating space, and an output part, and the openings and the output part are in spatial communication with the accommodating space. The main body unit corresponds to an inner wall of the accommodating space and protrudes toward the accommodating space to form a plurality of guiding parts, and each of the guiding parts is adjacent to one of the openings. The guide unit is disposed in the accommodating space and has a recessed part.

Therefore, one of the beneficial effects of the present disclosure is that, by virtue of "the nozzle module including a main body unit and a guide unit", "the main body unit being detachably connected to the nebulizer module", "the main body unit having a plurality of openings penetratingly formed through the main body unit, an accommodating space, and an output part, and the openings and the output part being in spatial communication with the accommodating space", "the main body unit corresponding to an inner wall of the accommodating space and protruding toward the accommodating space to form a plurality of guiding parts, and each of the guiding parts being adjacent to one of the openings", "the guide unit being disposed in the accommodating space and having a recessed part", and "the control module being detachably connected to the main body unit", the nebulizer device and the nozzle module provided herein can reduce the aggregation, collision, and condensation of atomized particles and improve the aerosol guiding efficiency.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Reference is made to FIG. 1 to FIG. 6, which are respectively an exploded view of a nebulizer device, an exploded view of a nozzle module, a structural view of the nozzle module, a first schematic view of a flow trajectory of a gas and a pressure distribution, a second schematic view of the flow trajectory of the gas and the pressure distribution, and a schematic view of an injection trajectory of atomized particles of the nebulizer device according to a first embodiment of the present disclosure. As shown in the figures, the present disclosure provides a nebulizer device Z, which includes a nebulizer module 1, a nozzle module N, and a control module 2. The nebulizer module 1 can be an atomization component for accommodating and atomizing liquid, and the control module 2 can be a host for the nebulizer device, but are not limited thereto.

Figure 1:
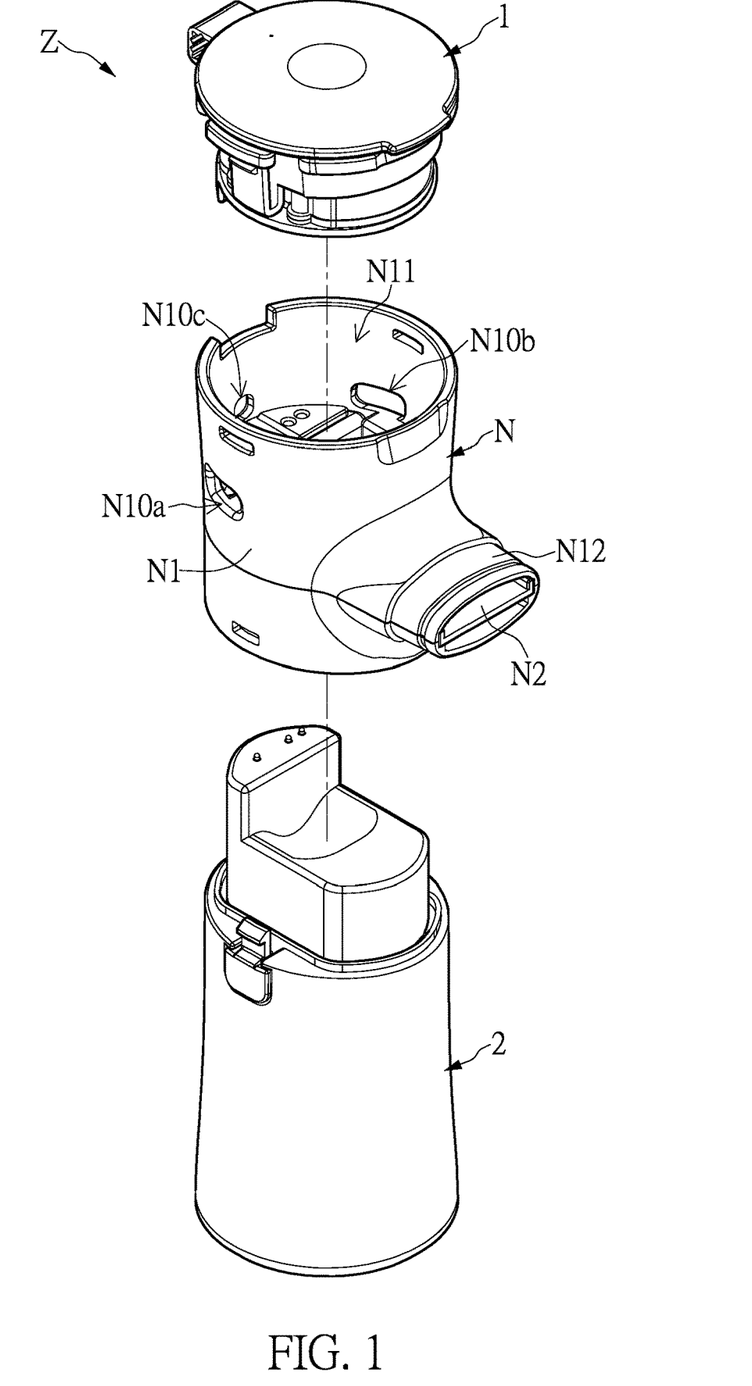
FIG. 1 is an exploded view of a nebulizer device according to a first embodiment of the present disclosure.
Figure 2:
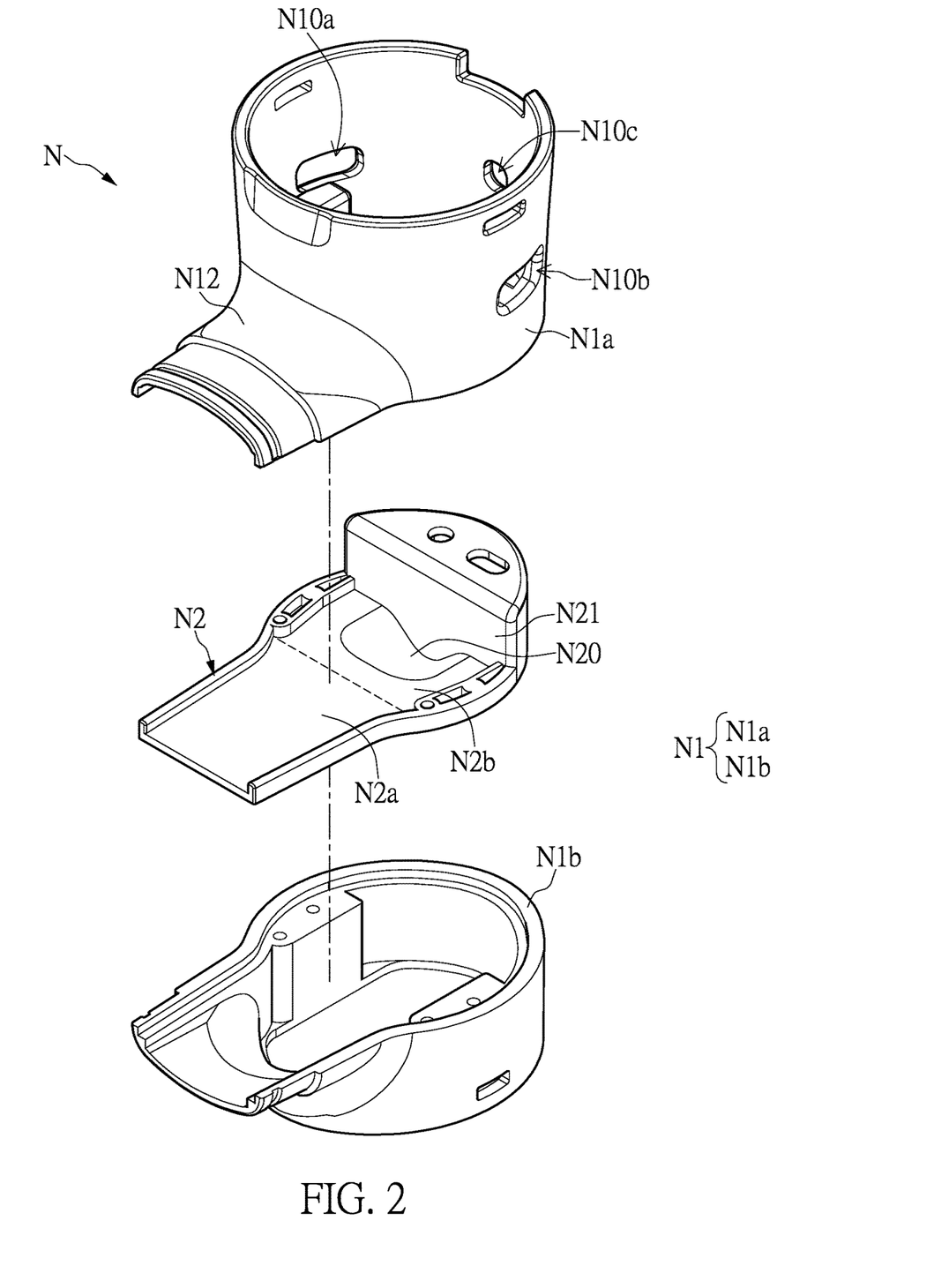
FIG. 2 is an exploded view of a nozzle module of the nebulizer device according to the first embodiment of the present disclosure.
Figure 3:
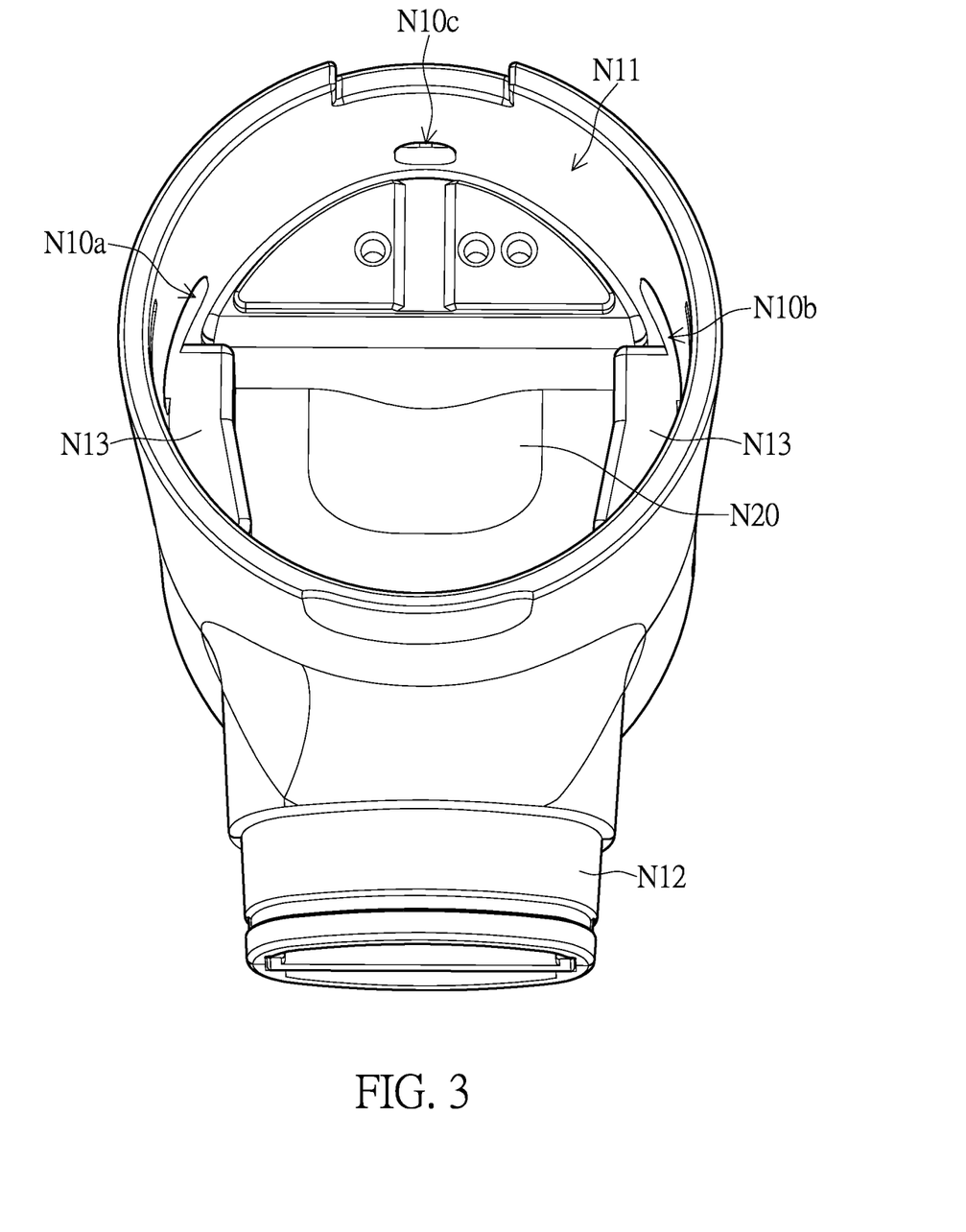
FIG. 3 is a structural view of the nozzle module of the nebulizer device according to the first embodiment of the present disclosure.

As shown in FIG. 1 and FIG. 2, the nozzle module N can include a main body unit N1 and a guide unit N2. For example, the main body unit N1 can be a casing structure; in this embodiment, the main body unit N1 is an example of a multi-piece structure. For example, the main body unit N1 includes a first main body N1a and a second main body N1b, the first main body N1a can be detachably connected to the second main body N1b, but is not limited thereto, and the main body unit N1 can also be a single component structure. The main body unit N1 can be detachably connected to the nebulizer module 1. Furthermore, as shown in FIG. 1 and FIG. 2, one end of the main body unit N1 can be detachably connected to the nebulizer module 1, and another end of the main body unit N1 can be detachably connected to the control module 2. The main body unit N1 can have a plurality of openings N10a, N10b, and N10c penetratingly formed through the main body unit N1, an accommodating space N11, and an output part N12, and the openings N10a, N10b, and N10c and the output part N12 are in spatial communication with the accommodating space N11. The openings N10a and N10b are located on both sides of the main body unit N1 and the opening N10c, the opening N10c is located on a rear side of the main body unit N1, and the output part N12 is located at a front side of the main body unit N1. More preferably, the opening N10a is disposed opposite to the opening N10b, and the opening N10c is disposed opposite to the output part N12, but it is not limited thereto.

As shown in FIG. 1 and FIG. 2, the guide unit N2 is disposed in the accommodating space N11 and has a recessed part N20. For example, the guide unit N2 can be a long plate-shaped structure and can be divided into a first area N2a and a second area N2b. The first area N2a can correspond to the output part N12, and the second area N2b can correspond to the accommodating space N11, but it is not limited thereto. The second area N2b of the guide unit N2 can be recessed to form the recessed part N20.

Therefore, as shown in FIG. 1 to FIG. 6, FIG. 4 and FIG. 5 show that flow trajectories of gas and gas flow in the nozzle module N have a plurality of different pressure distributions P1, P2, P3, P4, P5, P6, P7, P8, and P9. When the nebulizer module 1 provides atomized particles (such as atomized distilled water, physiological saline, artificial tears, medicinal solution, drug suspension, biologics, etc.) into the accommodating space N11, a first gas introduced through a portion of the openings N10a and N10b forms a first gas flow on the guide unit N2 and the recessed part N20 (the pressure distributions P1 and P2 in FIG. 4 and FIG. 5), that is, a high-pressure flow field vortex is formed. A second gas (the pressure distribution P2 in FIG. 4 and FIG. 5) introduced through another one of the openings N10c enters the accommodating space N11, and an interaction between the first gas flow and the second gas generates a second gas flow having a directional high and low pressure difference and a relatively low pressure being lower than a pressure of the first gas flow (the pressure distributions P3, P4, P5, P6, P7, P8, and P9 in FIG. 4 and FIG. 5). At the same time, the flow trajectory of the second gas flow guides the atomized particles to move in a direction of the output part N12 to deliver the atomized particles to an outside of the nozzle module N via the output part N12. Moreover, in conjunction with the injection trajectory V of the atomized particles shown in FIG. 6, the atomized particles are guided by the first gas flow and the second gas flow to move smoothly in a direction of a nozzle without flowing downwards.

Figure 4:
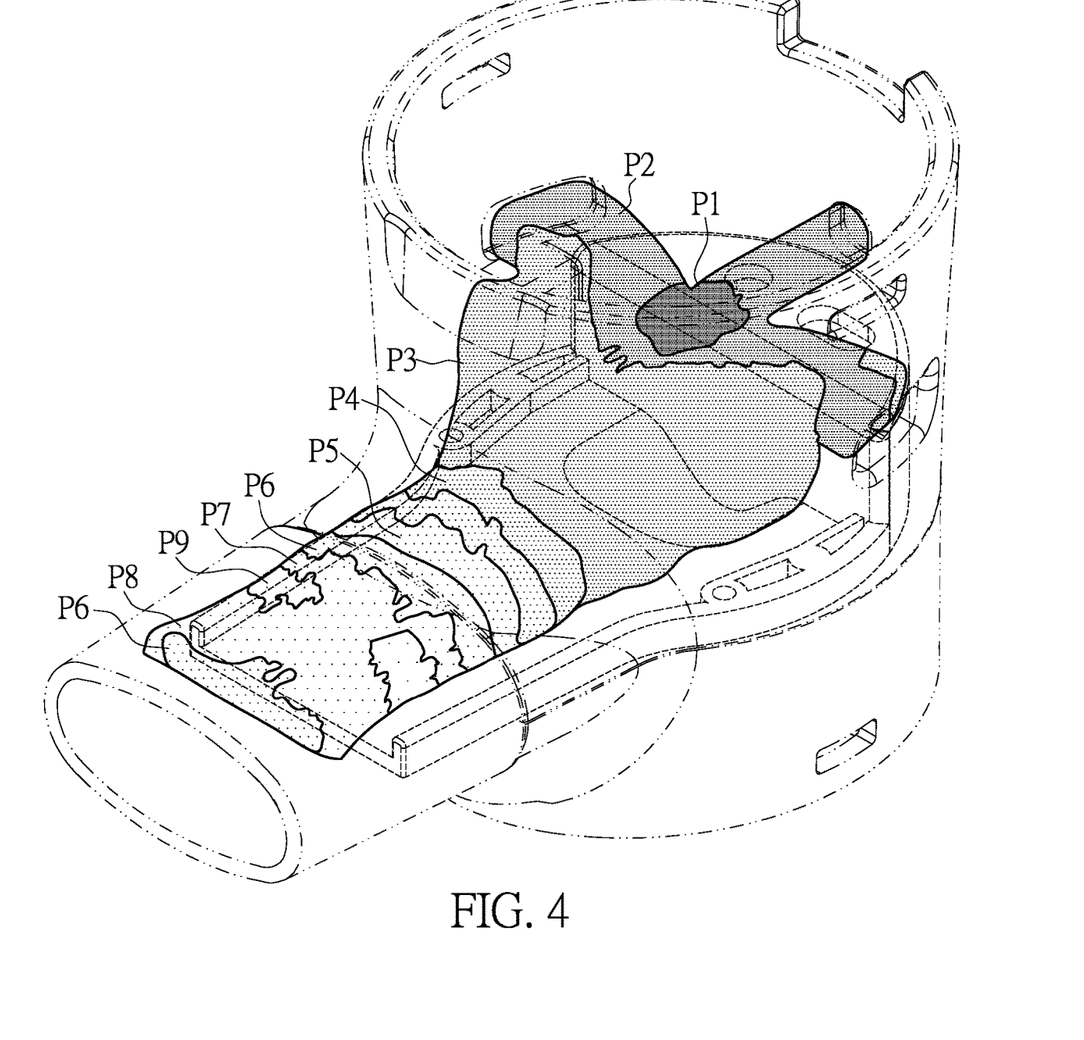
FIG. 4 is a first schematic view of a flow trajectory of a gas and a pressure distribution of the nebulizer device according to the first embodiment of the present disclosure.
Figure 5:
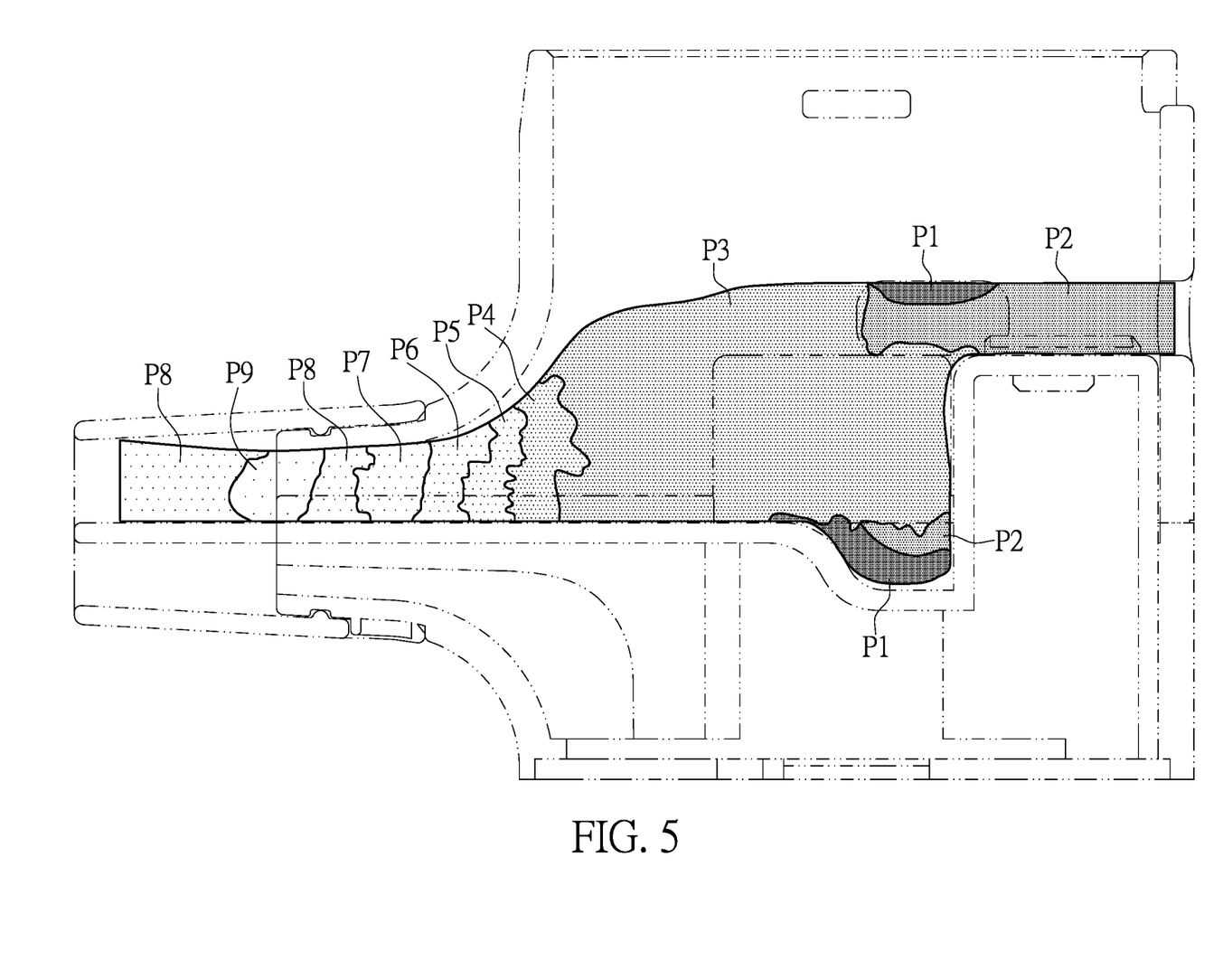
FIG. 5 is a second schematic view of the flow trajectory of the gas and the pressure distribution of the nebulizer device according to the first embodiment of the present disclosure.
Figure 6:
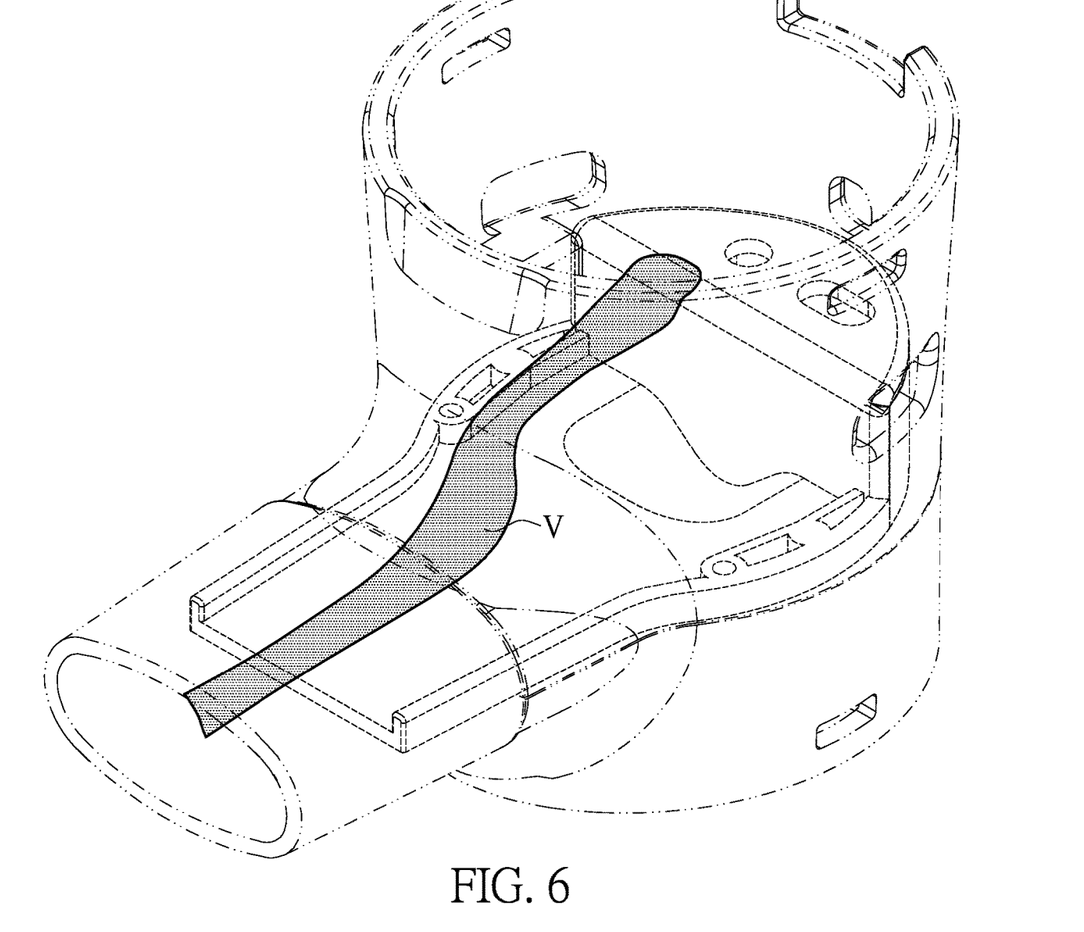
FIG. 6 is a schematic view of an injection trajectory of atomized particles of the nebulizer device according to the first embodiment of the present disclosure.

In addition, the simulations of the pressure distributions are as shown in FIG. 4 and FIG. 5. The pressure distribution P1 can be between 101316.76 Pa to 101319.80 Pa, the pressure distribution P2 can be between 101313.72 Pa to 101316.76 Pa, the pressure distribution P3 can be between 101310.67 Pa to 101313.72 Pa, the pressure distribution P4 can be between 101307.63 Pa to 101310.67 Pa, the pressure distribution P5 can be between 101304.59 Pa to 101307.63 Pa, the pressure distribution P6 can be between 101301.55 Pa to 101304.59 Pa, the pressure distribution P7 can be between 101298.51 Pa to 101301.55 Pa, the pressure distribution P8 can be between 101295.47 Pa to 101298.51 Pa, and the pressure distribution P9 can be between 101292.43 Pa to 101295.47 Pa, but are not limited thereto.

Accordingly, the nebulizer device Z of the present disclosure adopts the abovementioned technical solution to form the high-pressure flow field vortex (that is, the first gas flow) on the guide unit N2 and the recessed part N20 via the first gas introduced through the portion of the openings N10a and N10b, the second gas introduced through the another one of the openings N10c interacts with the first gas flow to generate the second gas flow having the directional high and low pressure difference and the relatively low pressure being lower than the pressure of the first gas flow, and the nebulizer device Z drives the nebulizer module 1 to provide the atomized particles in the accommodating space N11 to move smoothly in the direction of the nozzle, so as to reduce the aggregation, collision, and condensation of the atomizing particles and improve the aerosol guiding efficiency.

In addition, according to what was mentioned above, the present disclosure further includes a nozzle module N, which includes a main body unit N1 and a guide unit N2. The main body unit N1 has a plurality of openings N10a, N10b, and N10c penetratingly formed through the main body unit N1, an accommodating space N11, and an output part N12, and the openings N10a, N10b, and N10c and the output part N12 are in spatial communication with the accommodating space N11. The guide unit N2 is disposed in the accommodating space N11 and has a recessed part N20.

However, the previously mentioned example is only one of the feasible embodiments and is not meant to limit the present disclosure.

Second Embodiment

Figure 7:
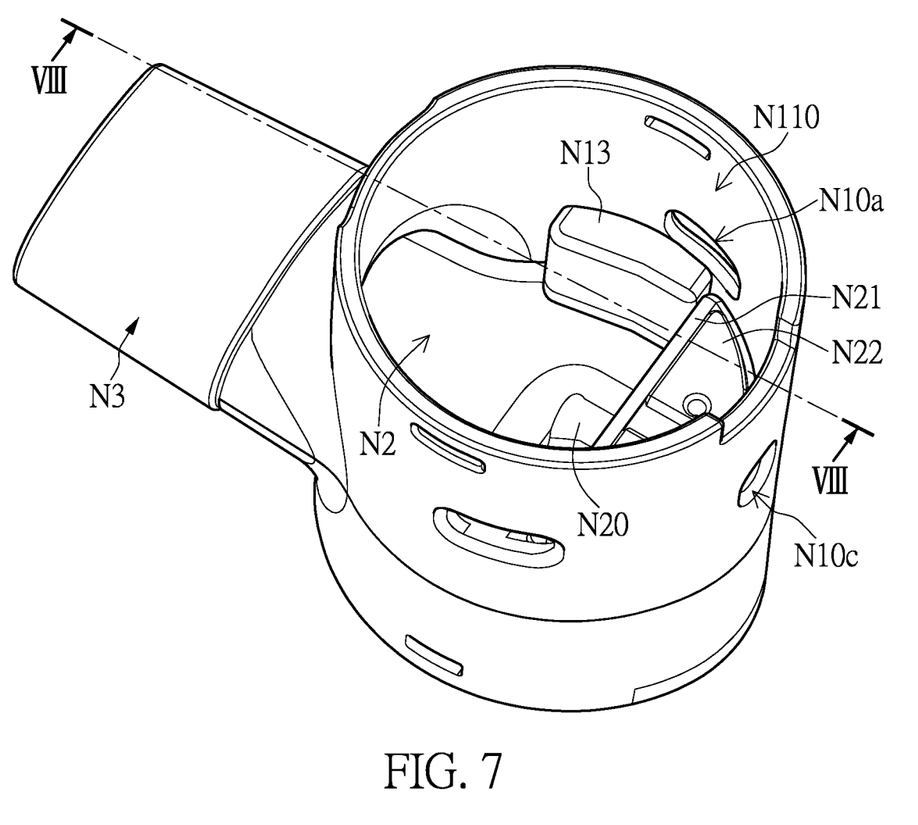
FIG. 7 is a structural view of the nozzle module of the nebulizer device according to a second embodiment of the present disclosure.

Reference is made to FIG. 7 to FIG. 10, which are respectively a structural view of the nozzle module of the nebulizer device, a cross-sectional view taken along line VIII-VIII of FIG. 7, an exploded view of the nebulizer device, and an exploded view of the nozzle module of the nebulizer device according to a second embodiment of the present disclosure, which are to be read in conjunction with FIG. 1 to FIG. 6. As shown in the figures, the same components of the nebulizer device Z of this embodiment and the nebulizer device Z of the abovementioned first embodiment operate in a similar manner, and will not be repeated herein. It is worth noting that in this embodiment, the guide unit N2 further has a protruding part N21, and the protruding part N21 is adjacent to the recessed part N20. The main body unit N1 corresponds to the inner wall of the accommodating space N11 and protrudes toward the accommodating space N11 to form a plurality of guiding parts N13, and each of the guiding parts N13 is adjacent to one of the openings N10a and N10b. The first gas forms the first gas flow between the protruding part N21, the recessed part N20, and the guiding parts N13.

Figure 8:
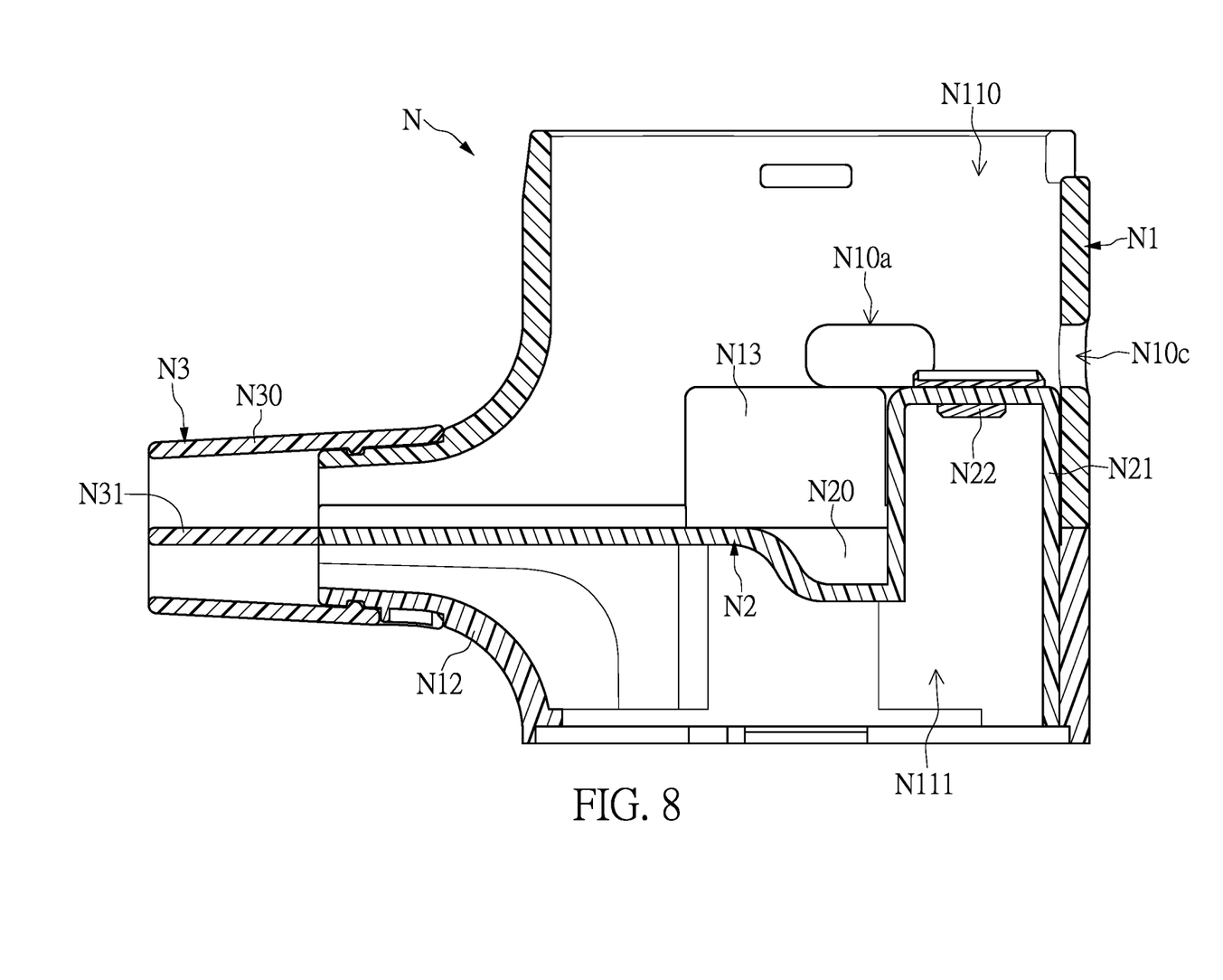
FIG. 8 is a cross-sectional view taken along line VIII-VIII of FIG. 7.
Figure 9:
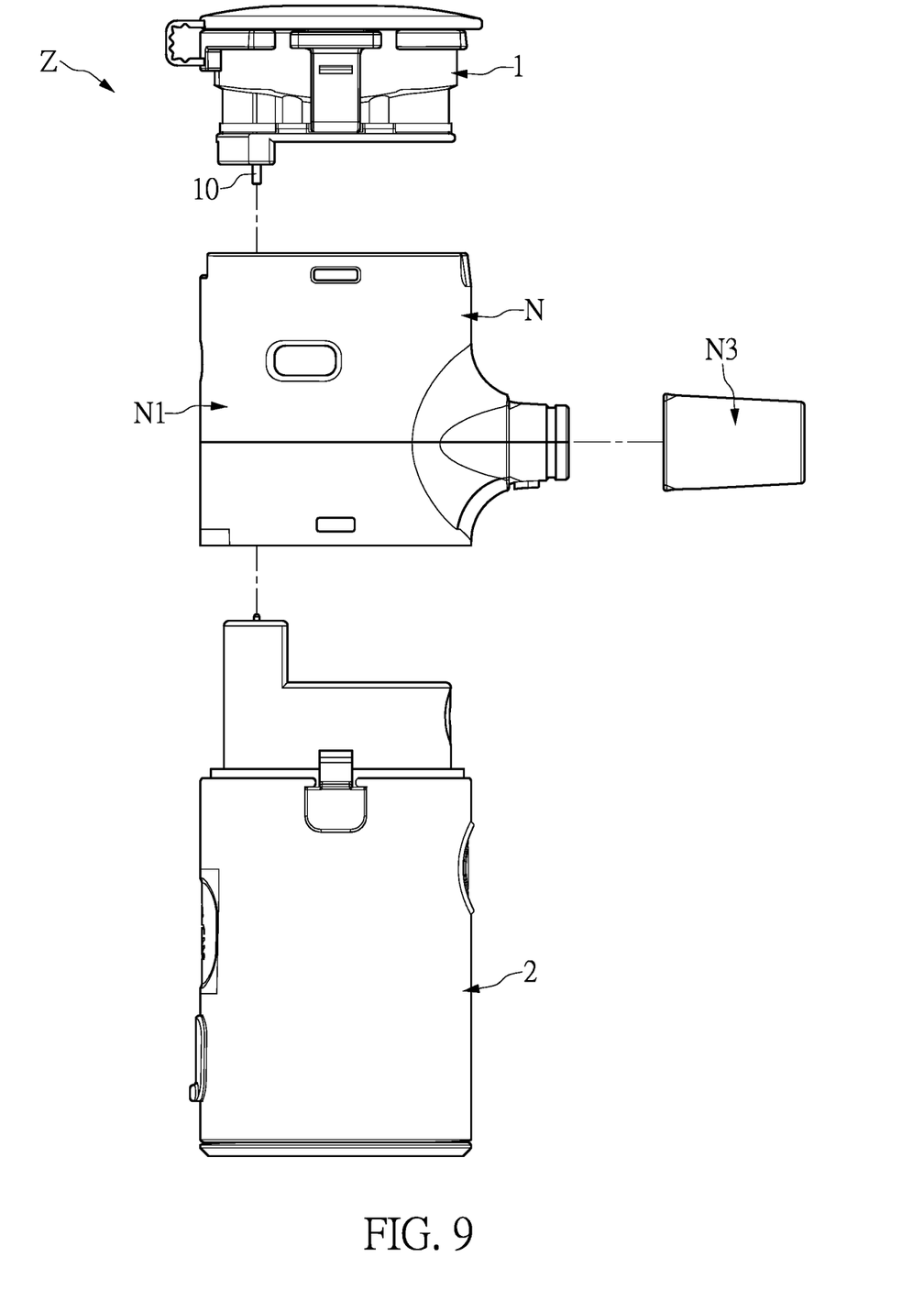
FIG. 9 is an exploded view of the nebulizer device according to the second embodiment of the present disclosure.
Figure 10:
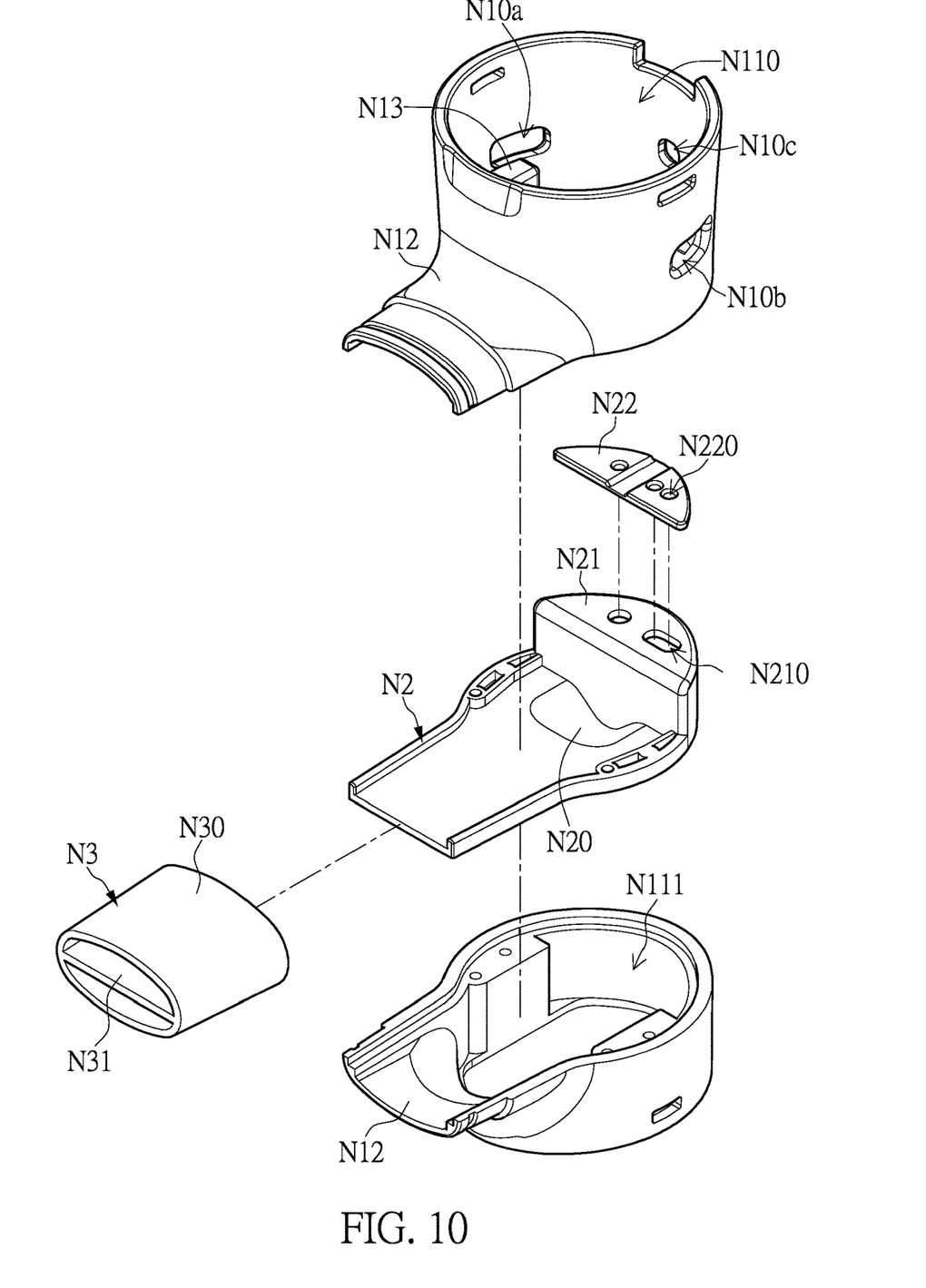
FIG. 10 is an exploded view of the nozzle module of the nebulizer device according to the second embodiment of the present disclosure.

For example, as shown in FIG. 7, FIG. 8, and FIG. 10, the protruding part N21 of the guide unit N2 can be located under the opening N10c. The inner wall of the main body unit N1 protrudes toward the accommodating space N11 to form the guiding parts N13. In this embodiment, the guiding parts N13 correspond to the openings N10a and N10b and are respectively located under the openings N10a and N10b, but it is not limited thereto. Furthermore, the guiding parts N13 can be oppositely disposed and located on both sides of the recessed part N20 or both sides of the protruding part N21, and the guiding parts N13 can be detachably connected to the guide unit N2. The recessed part N20 faces the nebulizer module 1, and the protruding part N21 is located between the recessed part N20 and the one of the openings N10c.

Therefore, as shown in FIG. 7, FIG. 8, and FIG. 10, when the first gas is introduced into the accommodating space N11 through the openings N10a and N10b, the first gas can form a vortex between the guiding parts N13, the protruding part N21, and the recessed part N20, so as to form a high-pressure flow field vortex (that is, the first gas flow).

Moreover, as shown in FIG. 7, FIG. 8, and FIG. 10, the guide unit N2 can divide the accommodating space N11 into a first space N110 and a second space N111, the first space N110 corresponds to the nebulizer module 1, and the second space N111 corresponds to the control module 2. Moreover, the first gas is introduced into the first space N110 through the portion of the openings N10a and N10b, and the first gas flow is formed between the guiding parts N13, the protruding part N21, and the recessed part N20. The second gas is introduced into the first space N110 through the another one of the openings N10c, and the second gas interacts with the first gas flow to form the second gas flow.

Furthermore, the protruding part N21 has a plurality of first through holes N210, the nebulizer module 1 has a plurality of pin parts 10, and each of the pin parts 10 inserts through the corresponding first through holes N210 and is connected to the control module 2. For example, as shown in FIG. 7 to FIG. 10, the first through holes N210 on the protruding part N21 can provide the pin parts 10 of the nebulizer module 1 to be inserted therethrough. The guide unit N2 can further include a gasket unit N22, the gasket unit N22 can be a waterproof rubber gasket, but the present disclosure is not limited thereto. The gasket unit N22 can be inserted through the first through holes N210 and located between the protruding part N21 and the nebulizer module 1. The gasket unit N22 has a plurality of second through holes N220, and the pin parts 10 of the nebulizer module 1 can be inserted through the second through holes N220. In addition, the nozzle module N further includes a nozzle unit N3, which is detachably connected to the output part N12. The nozzle unit N3 includes a junction part N30 and a divider part N31, and the junction part N30 can be detachably sleeved on the output part N12. Also, the divider part N31 is located inside of the junction part N30, and is parallel and opposite to the guide unit N2. Therefore, the guide unit N2 of the present disclosure can be a structure without any electronic components and circuits, and can be used to prevent the atomized particles provided by the nebulizer module 1 from colliding and condensing into liquid droplets and reaching the control module 2, resulting in the control module 2 being dampened and damaged by moisture.

However, the abovementioned example is only one of the feasible embodiments and is not meant to limit the scope of the present disclosure.

Beneficial Effects of the Embodiments

In conclusion, one of the beneficial effects of the present disclosure is that, by virtue of "the nozzle module N including a main body unit N1 and a guide unit N2", "the main body unit N1 being detachably connected to the nebulizer module 1", "the main body unit N1 having a plurality of openings N10a, N10b, and N10c, an accommodating space N11, and an output part 12 penetratingly formed through the main body unit N1, and the openings N10a, N10b, and N10c and the output part N12 being in spatial communication with the accommodating space N11", "

wherein a first gas is introduced through a portion of the openings and forms a first gas flow in the recessed part, and a second gas introduced through another one of the openings and the first gas flow form a second gas flow in the accommodating space;

wherein, when the nebulizer module provides at least one of atomized particles into the accommodating space, the at least one of atomized particles is guided to the output part by the second air flow, so as to deliver the at least one of atomized particles to an outside of the nozzle module via the output part.

10. The nozzle module according to claim 9, wherein the main body unit corresponds to an inner wall of the accommodating space and protrudes toward the accommodating space to form a plurality of guiding parts, and each of the guiding parts is adjacent to one of the openings.

11. The nozzle module according to claim 10, wherein the nozzle module further comprises a nozzle unit detachably connected to the output part.

12. The nozzle module according to claim 10, wherein the guiding parts are oppositely disposed and located on both sides of the recessed part or both sides of the protruding part, and the guiding parts are detachably connected to the guide unit; wherein the protruding part is located between the recessed part and the one of the openings.

13. The nozzle module according to claim 11, wherein the guide unit divides the accommodating space into a first space and a second space.

14. The nozzle module according to claim 13, wherein the first gas is introduced into the first space through the portion of the openings, and the first gas flow is formed between the protruding part, the recessed part, and the guiding parts, and wherein the second gas is introduced into the first space through the another one of the openings, and the second gas interacts with the first gas flow to form the second gas flow.

* * * * *